(12) United States Patent
Ratcliff

(10) Patent No.: US 11,523,605 B2
(45) Date of Patent: **\*Dec. 13, 2022**

(54) COMBINATION SCENT ROLLING APPLICATOR AND STORAGE CONTAINER

(71) Applicant: Michael Ratcliff, Rensselaer, IN (US)

(72) Inventor: Michael Ratcliff, Rensselaer, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/780,028

(22) Filed: Feb. 3, 2020

(65) Prior Publication Data

US 2020/0170239 A1 Jun. 4, 2020

Related U.S. Application Data

(63) Continuation-in-part of application No. 15/938,494, filed on Mar. 28, 2018, now Pat. No. 10,588,312.

(51) Int. Cl.
*B05C 11/105* (2006.01)
*A01M 31/00* (2006.01)
*A61L 9/12* (2006.01)

(52) U.S. Cl.
CPC .......... *A01M 31/008* (2013.01); *A61L 9/125* (2013.01); *A61L 9/127* (2013.01); *A61L 2209/134* (2013.01); *A61L 2209/15* (2013.01)

(58) Field of Classification Search
CPC ..................... A01M 31/008; B05C 11/105
See application file for complete search history.

(56) References Cited

U.S. PATENT DOCUMENTS

| 7,631,814 | B2* | 12/2009 | Zarembinski | A61L 9/12 239/53 |
| 9,185,901 | B1* | 11/2015 | Arcia | A01M 31/008 |
| 2003/0080197 | A1* | 5/2003 | Tuomikoski | A61L 9/12 239/44 |
| 2011/0088634 | A1* | 4/2011 | Shirley | A01K 15/025 119/708 |
| 2013/0015261 | A1* | 1/2013 | Scarbrough | A61L 9/03 239/34 |
| 2016/0120168 | A1* | 5/2016 | Blaha | A01M 31/008 239/56 |

\* cited by examiner

*Primary Examiner* — Jennifer C Chiang
(74) *Attorney, Agent, or Firm* — Gutwein Law; Tyler B. Droste

(57) ABSTRACT

A scent distribution device having a spherical housing and having one or more internal cavities in communication with a plurality of wicking members. The wicking members dispersed across the exterior of the housing for the distribution of a scent agent. The device including a harness engaged with an axis of the housing, wherein the housing rotates along the axis for rolling across a surface. The device further including a lead line and segregated and compartmentalized storage container.

20 Claims, 8 Drawing Sheets

COMBINATION SCENT ROLLING APPLICATOR AND STORAGE CONTAINER

CROSS-REFERENCE TO RELATED APPLICATION

This U.S. Patent Application claims priority to U.S. Non-provisional application Ser. No. 15/938,494 filed Mar. 28, 2018, which claims priority to U.S. Provisional Application No. 62/477,472 filed Mar. 28, 2017, the disclosure of which is considered part of the disclosure of this application and is hereby incorporated by reference in its entirety.

FIELD OF THE INVENTION

The present invention relates to an improved scent distribution device for hunting and a storage container for the distribution device.

BACKGROUND

The use of attractive scents when hunting has long been utilized as a device to attract desired game animals to a hunting location. Several types of devices and systems have been developed to aid hunters in the distribution of these scents. One such device designed to lure animals to a hunting site is a scent drag, trail drag, or drag rag, as it is often called. A typical scent drag is comprised of an absorbent based material saturated with a liquid based attractive scent and attached to a string-like member for dragging or pulling across a ground surface to deposit the scent along the surface with the hope of attracting and leading an animal to a designated area.

U.S. Pat. No. 6,880,765 discloses one type of scent lure in the form of a spherical ball. This ball provides for a pair of hemispheres separable and designed for the placement of a liquid scent to a wicking surface contained within the interior of the sphere. Perforations within the spherical body allow for the release of the liquid within the sphere and a tab member allows for engagement with a hanger to hang the lure during use.

Although devices of this type are operable to distribute a scent to an area upon hanging, they are not adapted for dragging across a surface, providing a wide patterned distribution of a scent, adapted for engagement with replacement wicks, and provided with an integrated and segregated carry device.

Therefore, there is a need for an improved scent distribution device that is adapted for rolling transport along a ground surface, durable, designed for the engagement of replaceable wick members, and provided with a specific carry and storage member.

BRIEF SUMMARY OF THE INVENTION

The device of the present invention relates to a new and improved scent applicator to lure an animal to a desired area. The device of the present invention is generally spherical in shape and designed with a pair of interior cavities positioned on the opposed hemispheres of the sphere for the placement of a liquid scent to be distributed to an external area of the device. The scent material is distributed from the pair of interior cavities through a plurality of removable and replaceable wicking members that extend from the interior of the device to the exterior of device extending outward from the device in a multitude of projections for distributing the scent material.

The device includes a swivel harness in communication with an axle member positioned at the equatorial axis of the spherical device, wherein the device is capable of rotation along this axis and wherein the harness is capable of movement along the axle coupling to allow for both rotational movement of the harness and sphere during use.

The device includes a removable lead member with a pair of opposed clip members at each end of the length of the lead to allow for attachment of the lead to the harness and to a user of the device, wherein the device can be pulled or dragged along a surface without the use of the user's hands. Preferably, the clip members are provided with a rotational swivel member to allow for rotation in a direction perpendicular to the length of the lead to prevent tangling of the lead during use.

The device further includes a storage container specifically designed and adapted for use with the device. The storage container is generally provided in a durable air tight and watertight material and segregated into two distinct compartments; one compartment for receiving the ball; and one compartment for receiving the lead. These separate compartments are designed to prevent cross contamination of scents from the ball to the lead and from both of the items to a user. Preferably, this storage container includes a clip member to allow for easy attachment to a user or carry article of the user for easy storage and transport of the device.

BRIEF DESCRIPTION OF THE DRAWINGS

The accompanying drawings are included to provide a further understanding of the present invention and are incorporated in and constitute a part of this specification with the description serve to further explain the principles of the invention. Other aspects of the invention and the advantages of the invention will be better appreciated as they become better understood by reference to the Detailed Description when considered in conjunction with accompanying drawings, and wherein.

DETAILED DESCRIPTION OF THE INVENTION

Figure 1:
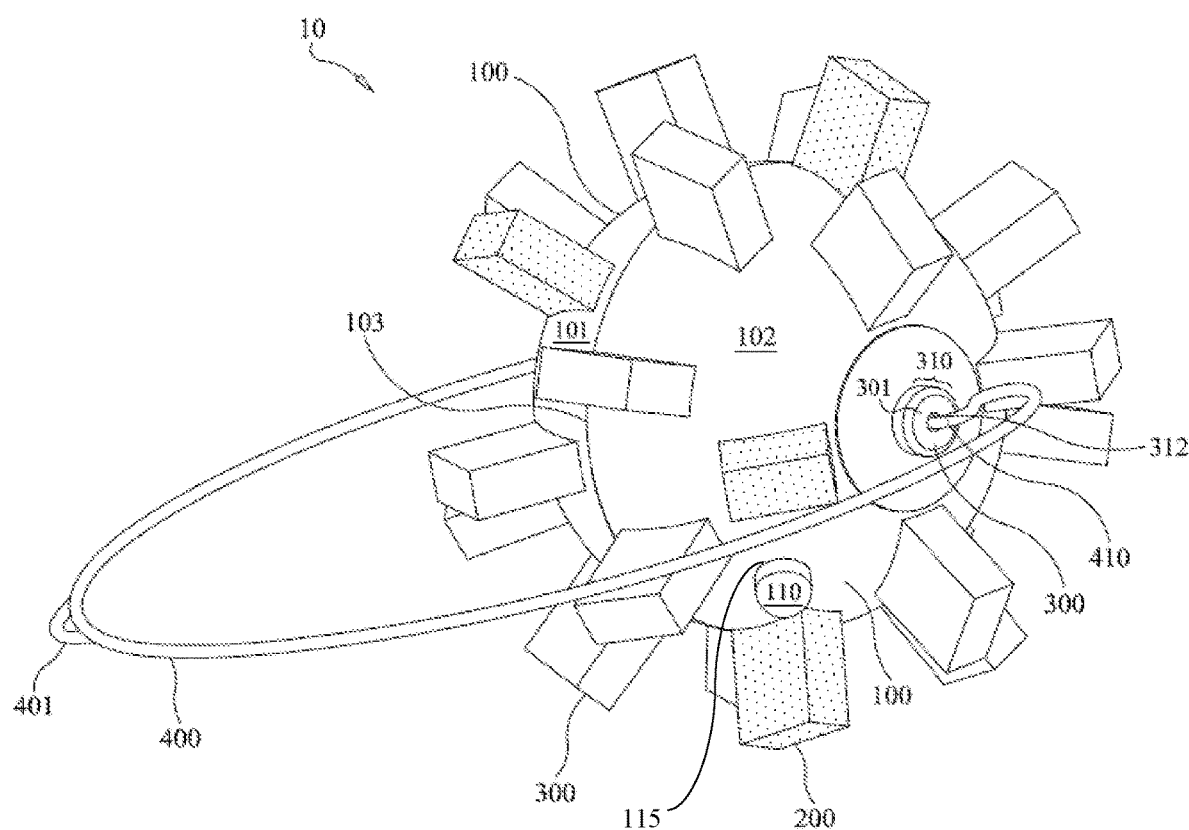
FIG. 1 is an isometric view of the scent rolling applicator, according to the present disclosure.
Figure 2:
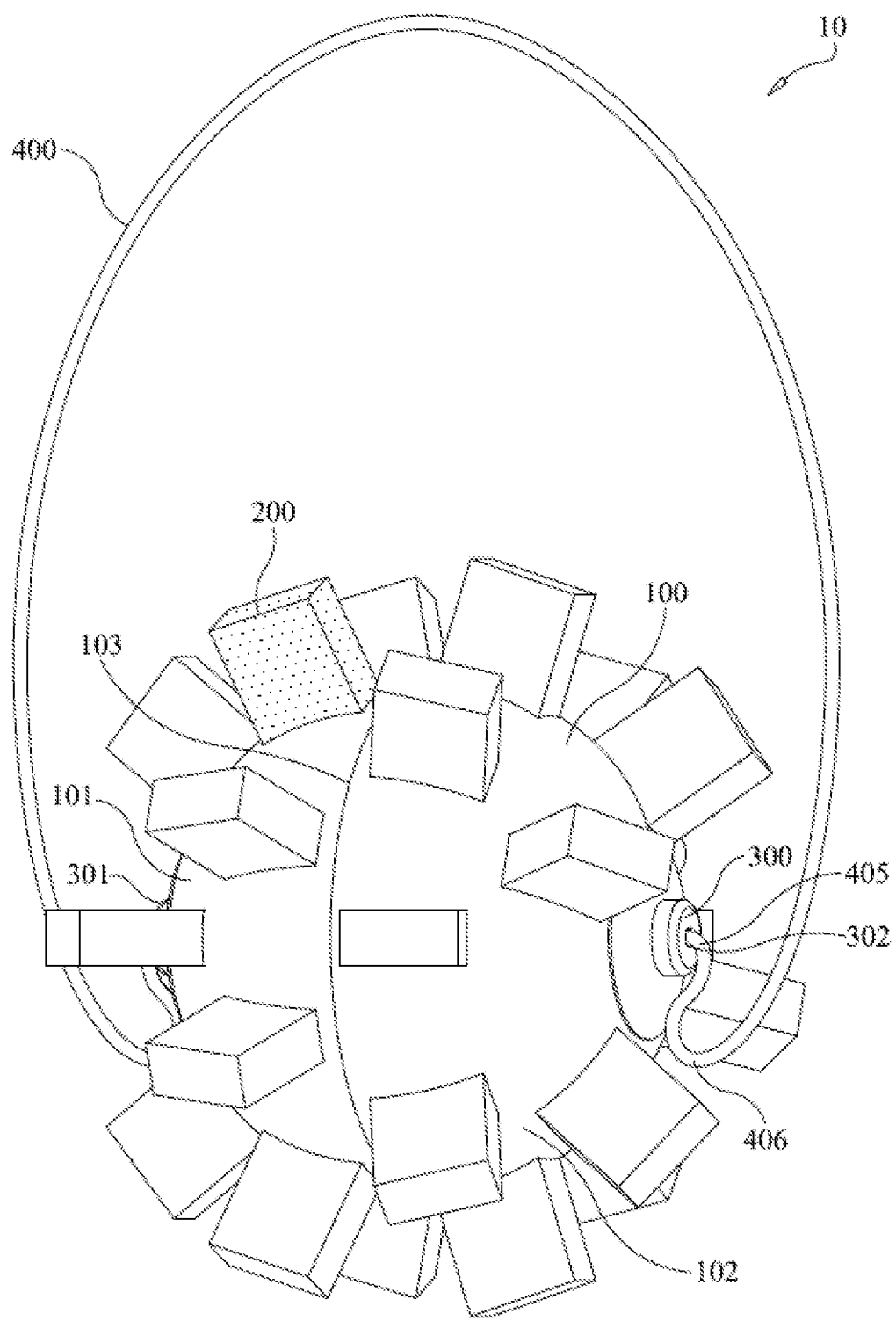
FIG. 2 is another isometric view of the scent rolling applicator, according to the present disclosure.

The following detailed description includes references to the accompanying drawing, which forms a part of the detailed description. The drawing shows, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, and logical changes may be made without departing from the scope of the present invention. The following detailed description is, therefore, not to be taken in a limiting sense.

Before the present invention is described in such detail, however, it is to be understood that this invention is not limited to particular variations set forth and may, of course, vary. Various changes may be made to the invention described and equivalents may be substituted without departing from the true spirit and scope of the invention. In addition, many modifications may be made to adapt a particular situation, material, composition of matter, process, process act(s) or step(s), to the objective(s), spirit or scope of the present invention. All such modifications are intended to be within the scope of the disclosure made herein.

Unless otherwise indicated, the words and phrases presented in this document have their ordinary meanings to one of skill in the art. Such ordinary meanings can be obtained by reference to their use in the art and by reference to general and scientific dictionaries.

References in the specification to "one embodiment" indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following explanations of certain terms are meant to be illustrative rather than exhaustive. These terms have their ordinary meanings given by usage in the art and in addition include the following explanations.

As used herein, the term "and/or" refers to any 5 one of the items, any combination of the items, or all of the items with which this term is associated.

As used herein, the singular forms "a," "an," and "the" include plural reference unless the context clearly dictates otherwise.

As used herein, the terms "include," "for example," "such as," and the like are used illustratively and are not intended to limit the present invention.

As used herein, the terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the terms "front," "back," "rear," "upper," "lower," "right," and "left" in this description are merely used to identify the various elements as they are oriented in the FIGS, with "front," "back," and "rear" being relative to the apparatus. These terms are not meant to limit the elements that they describe, as the various elements may be oriented differently in various applications.

As used herein, the term "coupled" means the joining of two members directly or indirectly to one another. Such joining may be stationary in nature or movable in nature. Such joining may be achieved with the two members or the two members and any additional intermediate members being integrally formed as a single unitary body with one another or with the two members or the two members and any additional intermediate members being attached to one another. Such joining may be permanent in nature or alternatively may be removable or releasable in nature.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element without departing from the teachings of the disclosure.

Figure 7:
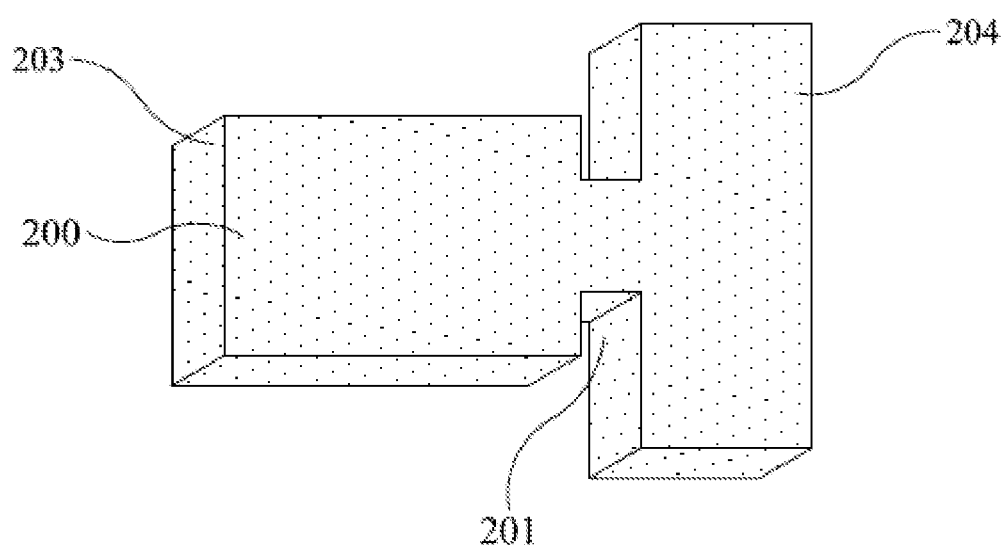
FIG. 7 is perspective view of a wicking member, according to the present disclosure.
Figure 8:
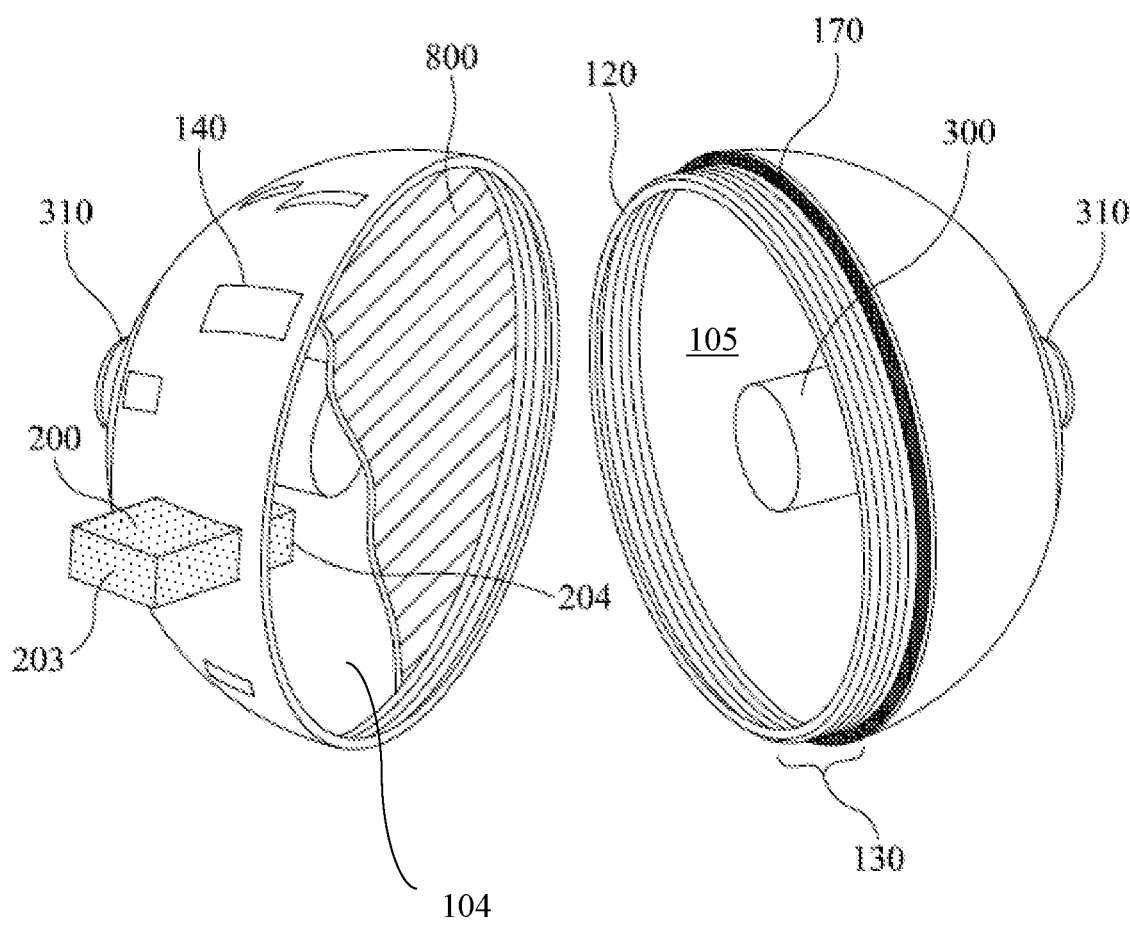
FIG. 8 is an isometric view of an exemplary embodiment of a scent rolling applicator according to the present disclosure having two removeably couplable hemispherical members.

Referring now to FIG. 1-FIG. 8, the scent rolling applicator of the present disclosure is shown and generally referred to as device 10. The device 10 of the present disclosure is generally designed for rolling along a surface for the distribution of an attractant scent to an area. Accordingly, the device 10 is generally comprised of a spherical housing 100 comprised of a pair of hemispheres 101, 102 with each hemisphere having an integrated internal cavity 150 for the placement of a liquid scent within this internal cavity. The hemispheres can be divided along a longitudinal plane 103. Access to the internal cavity 150 is controlled through one or more removable caps 110, 120 with each cap 110, 120 of the pair of caps received in an opposed hemisphere 101, 102 that can be easily removed and installed to allow for refilling of the internal cavities of the device 10. The caps 110, 120 can be configured to removeably seal a passage 115 from the exterior of housing 100 to the interior cavity 150. In one exemplary embodiment as illustrated in FIG. 8, the spherical housing 100 can include a plurality of cavities, such as a first cavity 104 and a second cavity 105, within the first hemisphere 101 and the second hemisphere 102. The same or different liquids can be placed in the cavities 104, 105. Alternatively, one cavity can be empty, while the other is filled with a liquid. The type and quantity of the liquid can be determined based upon a user's desired application. An interior wall 800 can separate the two interior cavities 104, 105.

The spherical housing 100 can include a plurality of apertures in the form of slots 140 distributed in an off-set pattern around the housing 100 and dispersed across each hemisphere 101, 102. The slots within the housing 100 are sized and shaped for the engagement of a wicking member 200 having a first portion 204 in communication with the one or more of the respective internal cavities and a second portion 203 extending from the exterior of the housing 100. The wicking member 200 can be configured to disperse liquid within the cavity to an external environment, wherein liquid placed within the internal cavity is absorbed by the wicking member 200 for dispersal to the exterior of the housing 100. In one exemplary embodiment, liquid within the cavity 150 can be dispersed from the first portion 204 to the second portion 203 on the exterior of the housing 100. As illustrated in FIG. 7, the wicking member 200 is preferably constructed out of a felt or felt-like material and generally T-shaped and having a pair of notches 201 sized for engagement with the slots 140. Similarly, the wicking member 200 can be made from any suitable material that can absorb and disperse the liquid from the interior of the cavity 150 to the exterior of the housing 100, such as a sponge, sponge-like material, linen, or cloth material. In a preferred embodiment of the apparatus of the present disclosure, the device 10 can include twenty-four slots for placement of the removable wicking members 200. Preferably, the wicking members 200 are provided in a thickness of about ¼ inch to about ⅜ inch with a length of about 1 and ¼ inches and a width of about 1 inch for engagement within slots having approximate dimensions of about ¼ inch 10 wide and about ⅜ inch long.

The device 10 further includes an axle member 300 disposed equatorially across the diameter of the spherical housing 100 along the hemispheres 101, 102 to provide for the attachment of a harness 400 on the opposed sides of the housing 100 to an axle member 300, wherein the housing 100 rotates around the axle member 300 for rolling or dragging across a surface. The axle member 300 can have a first end 301 and a second end 302. The axle member 300 can end equatorially across the entire diameter within the cavity of the housing 100. Alternatively, the axle member 300 can extend only partially within the cavity on each of the first end 301 and the second end 302, while still defining a central axis. In another exemplary embodiment, each hemisphere 101, 102 an axle member 300 can be formed by having a slight protrusion 310 extending out from the spherical housing. The protrusion can have a cavity 312 configured to couple to or allow for coupling of an end of the harness 400. This embodiment can limit the amount of space within the interior cavity of the housing 100 that the one or more axle members 300 occupies, thereby allowing for more liquid to be stored within the cavity. Alternatively, the cavities 312 can be formed on the first end 301 and second end 302 along the central axis on the exterior surface of the housing 100. The cavities 312 can be configured to accept a harness 400. In some exemplary embodiment, the protrusion can eliminate any interior protrusion into the interior cavity by the axle member thereby providing maximum capacity within the cavity of the housing. Other exemplary embodiments, can include an axle member 300 formed along an equatorially axis completely through the interior cavity of the housing. In such an embodiment, the harness 400 can be removeably coupled to the axle member 300 at the housing portion can rotate 360° around the axle member.

Figure 3:
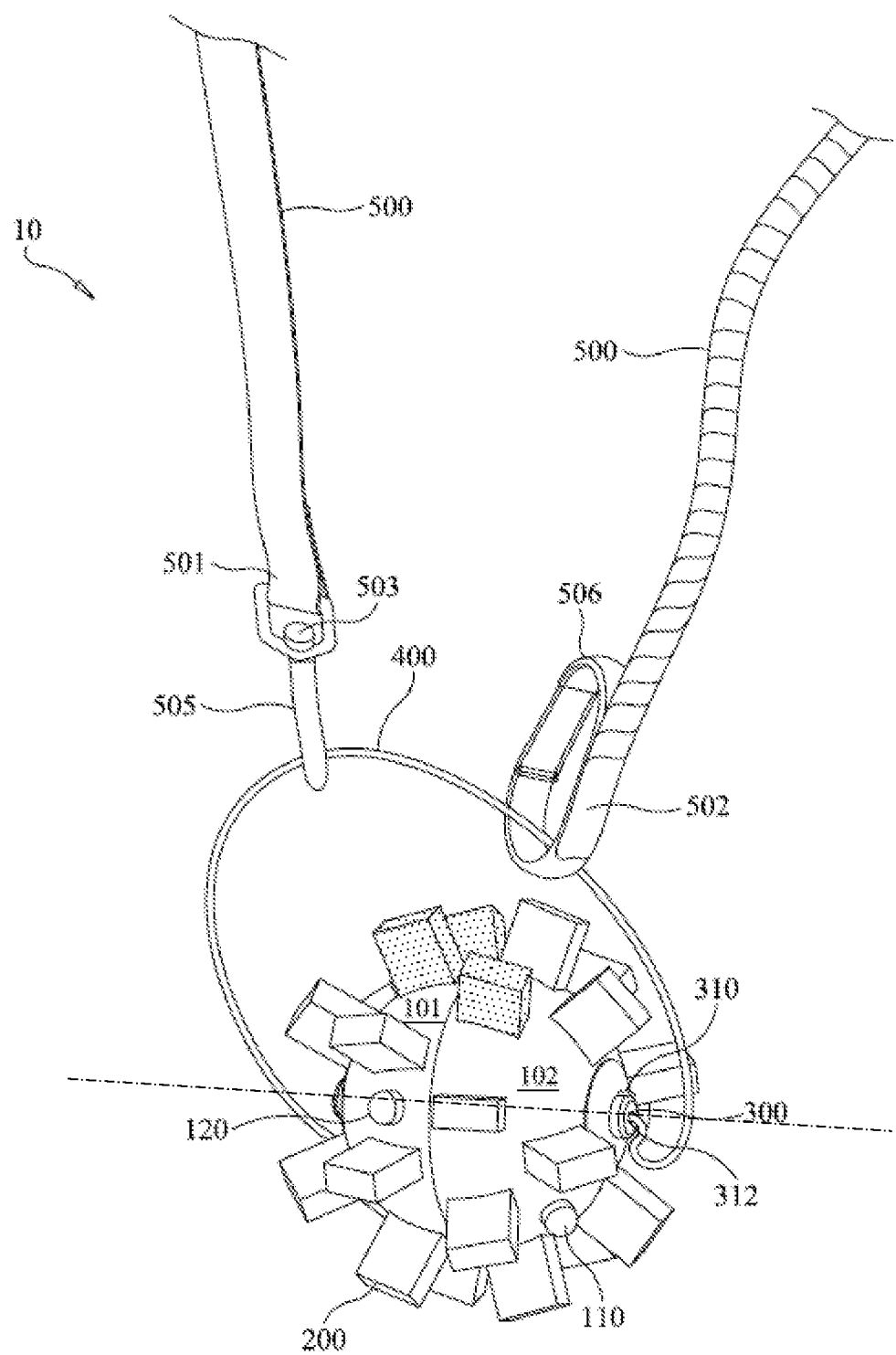
FIG. 3 is an isometric view of the scent rolling applicator having a lead line, according to the present disclosure.
Figure 4:
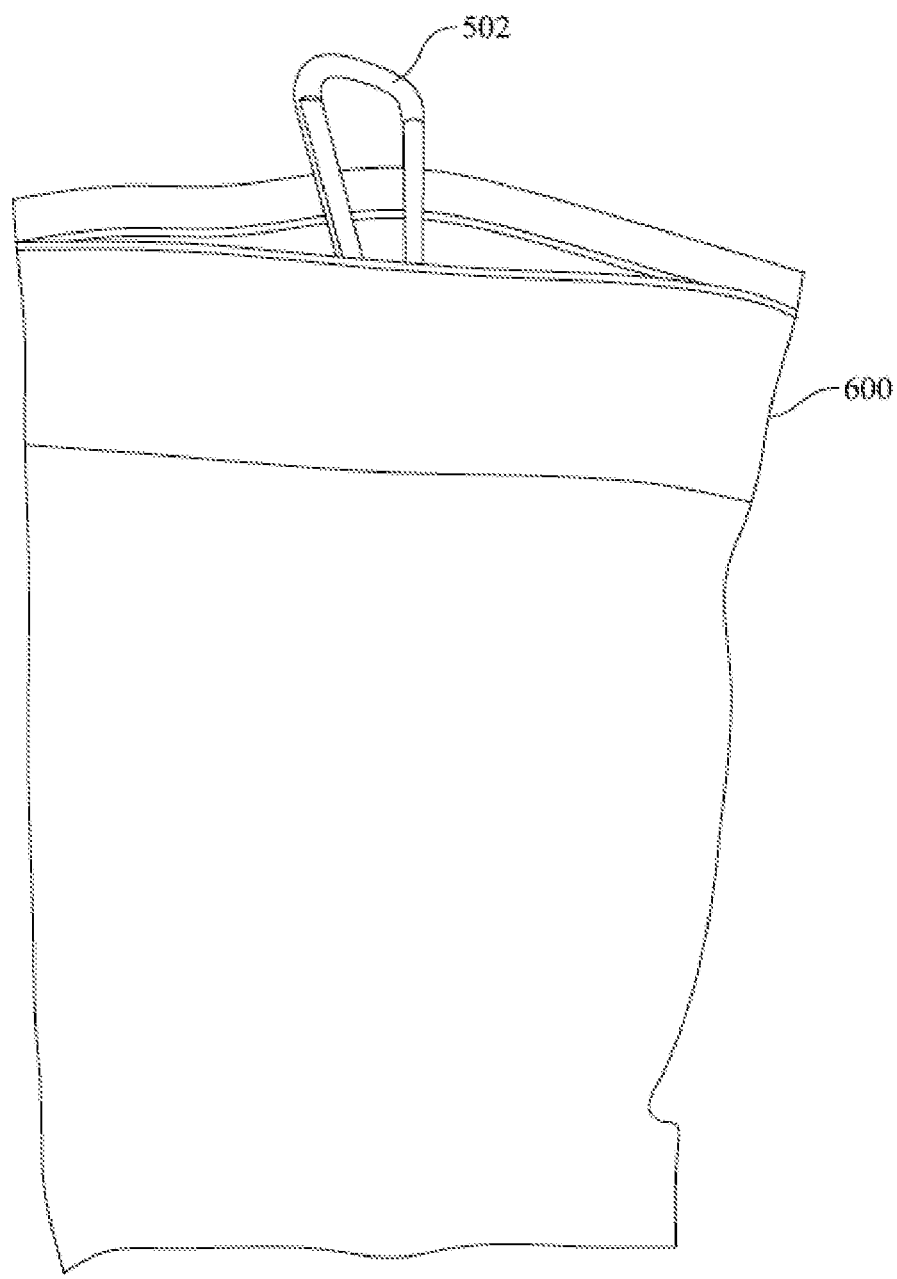
FIG. 4 is a side view of the scent rolling applicator with lead line within a storage container, according to the present disclosure.

As illustrated in FIG. 3, the harness 400 extends around half of the spherical housing 100 and includes a connecting portion 401 for attachment of a lead line 500. In one exemplary embodiment, the harness 400 can include a first curved portion 405 that extends from the axle member and a second curved portion 406 from the second curved portion 406 on one or both of the respective sides of the axle member. In one exemplary embodiment, the harness can be parabolic in shape to help cut through brush and other obstacles when being pulled by a user. In other embodiment, the harness 400 can include a coupling point or connection portion 401. The harness can also include a first end 410 and a second end 412, wherein the first end 410 terminates within the first end 301 cavity 312 of the axle member 300 and the second end 412 terminates within the second end 302 cavity 312. The first end 410 and second end 412 of the harness can operate as rotational points along the central axis to allow for the housing 100 to rotate along a center axis between the first end 410 and second end 412 of the harness. The housing 100 can be positionally centered between the first end 410 and second end 412. The harness can be configured in a parabolic shape between the first end 410 and the second end 412 to allow for enough clearance to allow the housing 100 and wicking member(s) 200 to freely rotate along the center axis without impeding the rotation of the housing 100. The cavities 312 can be positioned opposite one another along the central axis on the exterior surface of the housing or at the protrusions 310. Some exemplary embodiments of the harness 400 may be composed of any suitable material, such as a polymer or metal that can maintain its shape under a force, so as not to distort or warp and prevent the housing 100 from rotating between the first and second ends of the harness. A portion on each end of the harness 400 can extend into the cavities 312 to maintain the housing 100 within the harness 400 and to provide a rotational axis along which the housing can rotate 360° around the center axis.

The harness can be coupled to the housing 100 using any suitable means, such as a compression fit or fasteners. The harness 400 is configured to allow for the housing 100 to rotate around the central axis as the device 10 is dragged along the ground using the lead line 500. The various wicking members 200 can apply a scent to the surrounding area that contacts the wicking members 200 as the device is pulled by a user, thereby effectively providing scent liquid in the desired area without the need of continually reapplying a scent to a pad for reapplication. In some exemplary embodiments, a plurality of scents can be applied simultaneously by using different scents in each hemispherical cavity 150. Other embodiments can be comprised of a singular housing body, with a single internal cavity 150.

The lead line 500 of the device 10 is comprised of a pair of opposed ends 501, 502 having attachment members. One end 501 the attachment member 505 can couple to the harness 400, preferably in the form of clips, for attachment to the harness 400 or a user of the device 10. On the opposite end 502, the attachment member 505b can couple to a portion of the harness 400. Preferably, an end 501, 501 of the lead line 500 includes a an attachment member 505 can include a swivel connector 503 allowing for rotation of the attachment clip perpendicular to the direction of travel of the moving device 10 to allow for smooth rolling around the central axis and the prevention of tangling of the lead line 500. In some exemplary embodiment, the swivel connector can be a ball and socket swivel to allow for multi-axis direction of travel between the lead line 500 and the harness 400.

The device 10 further includes a storage container 600 specifically designed with segregated portions for the placement of the housing 100 and the lead line 500, wherein a user can prevent contamination during use. The storage container 600 is preferably constructed out of a waterproof and durable material and provided with a clip member for securing the container to user or other items for storage and carrying. The storage container 600 can have multiple compartments and be resealable to prevent or inhibit scent from escaping the container when the device 10 is not in operation.

Figure 5:
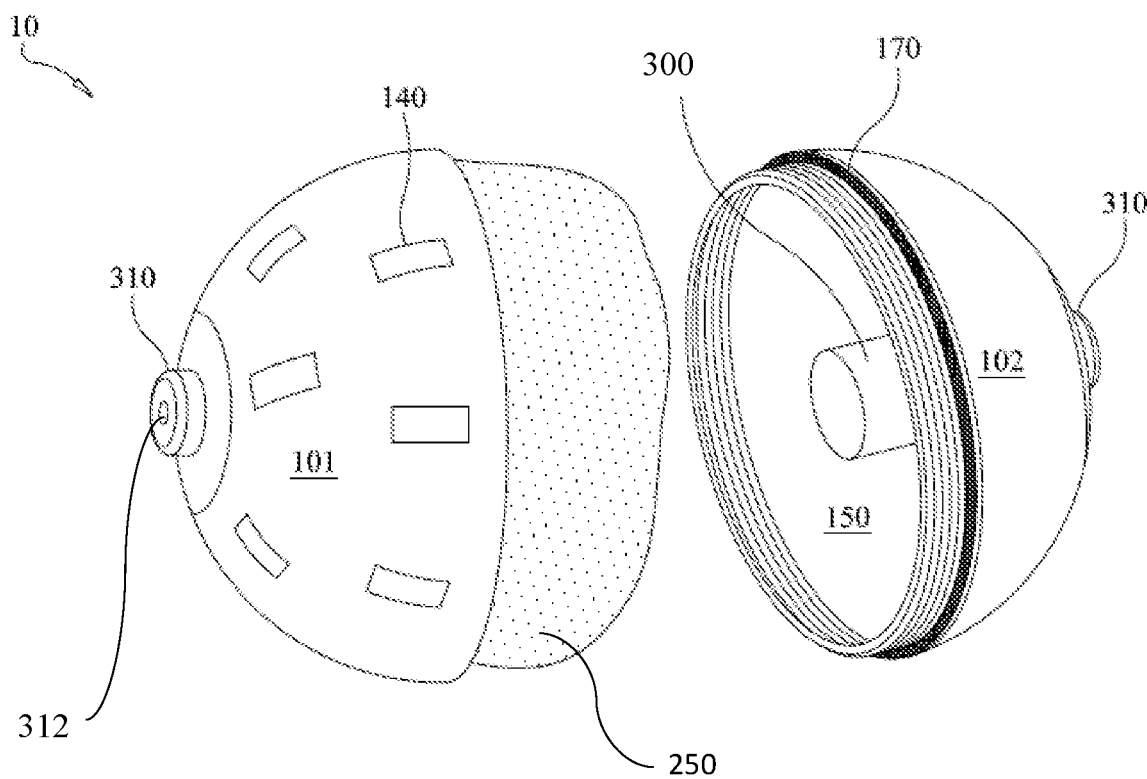
FIG. 5 is an isometric view of the scent rolling applicator having a threaded coupling means, according to the present disclosure.
Figure 6:
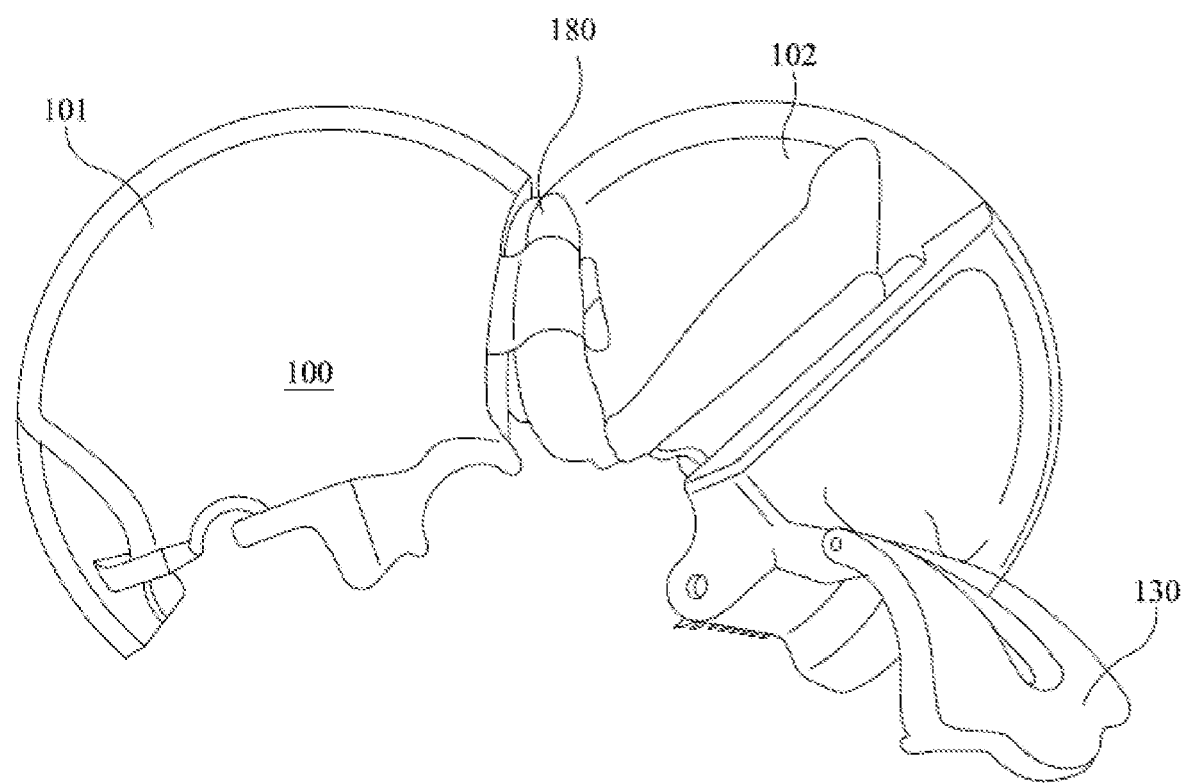
FIG. 6 is an isometric view of the scent rolling applicator having a hinged coupling means, according to the present disclosure.

Preferably, the housing 100 of the device 10 is provided in a diameter of about three inches and comprised of a resilient and durable material such as poly vinyl chloride (PVC) or other similar plastic or polymer material. Preferably, the lead line is provided in a length of about six feet. In some other exemplary embodiments, the first hemisphere 101 and second hemisphere 102 can be coupled together along a longitudinal plane 103 using any suitable coupling means. As illustrated in FIG. 5, some embodiments of the device 10 of the present disclosure can include a coupling means 130 can be comprised of corresponding threaded portions 130 along the perimeter edge 120 of each hemisphere 101, 102. A sealing means 170, such as a gasket, can be used to maintain a sealing relationship between the two hemispheres and maintain a liquid within the single cavity 150. The cavity 150 can contain a separate interior wicking member 250. The interior wicking member 250 can help maintain the liquid within the cavity 150 and limit the amount of liquid that exits through the slots 140. Another exemplary embodiment of the device 10 of the present disclosure can include a coupling means 130, such as a latch and further include a hinge 180 coupling the first hemisphere 101 and second hemisphere in a hinged relationship.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) but that the invention will include all embodiments falling with the scope of the specification.

What is claimed is:

1. A liquid application device, the liquid application device comprising:
    a housing, the housing having a first interior cavity, wherein the interior cavity provides a first reservoir for the placement of a liquid;
    a plurality of slots wherein the slots are configured to disperse the liquid from the interior cavity to an exterior of the housing;
    a harness comprising a first end and a second end, wherein the first end and second end are positioned opposite each one another along a center axis of the housing, wherein the housing is positioned between the first end and second end of the harness and configured to rotate around the center axis between the first end and second end of the harness.

2. The device as in claim 1, wherein device further comprises wick members, the wick members positioned within the plurality of slots, wherein the wicking members are in removable communication with the first interior cavity, wherein the wick members have first portion extending inside the cavity and a second portion extending from the exterior of the spherical housing, wherein the wick members are configured to further disperse the liquid from the interior cavity to the exterior of the housing.

3. The device as in claim 1, wherein the housing further comprises an external cap on the spherical housing configured to provide access into the interior cavity.

4. The device as in claim 1, wherein cavity includes an interior wicking member, wherein the interior wicking member is configured to maintain the liquid within the cavity and limit the amount of liquid that exits through the slot.

5. The device as claim 2, wherein the device includes a storage container.

6. The device as in claim 5, wherein the storage container contains a pair of segregated compartments.

7. The device as in claim 1, wherein the liquid is a scent agent.

8. The device as in claim 1, wherein the spherical housing comprises two internal cavities separated by an internal wall, wherein the first reservoir of the first cavity is accessed by a first cap, and the second reservoir of the second cavity is accessed by a second cap.

9. The device as in claim 8, further comprising an axle member, wherein the axle member is defined along the center axis, wherein the harness couples to the axis member to allow for rotation of the housing around the center axis.

10. The device as in claim 9, wherein the harness is substantially parabolic in shape and configured to allow for the housing and wicking members to freely rotate along the center axis.

11. An apparatus for storing and applying a liquid, comprising:
    a housing, wherein the housing comprises an internal cavity configured to provide a reservoir for the placement of a liquid;
    at least one slot to configured to disperse the liquid within the internal cavity;
    a harness coupled to the housing, wherein the harness is configured to allow for the housing to spin freely along an equatorial axis.

12. The apparatus of claim 11, further comprising a wicking member configured to be removeably coupled to the slot, where a first portion of the wicking member is located within the cavity and a second portion is located on the exterior of the housing.

13. The apparatus of claim 12, wherein the housing comprises an axle member.

14. The apparatus of claim 13, wherein the axle member is comprised of a first protrusion having a first cavity on one side of the housing, and a second protrusion having a second cavity on the opposite side of the housing along the equatorial axis, wherein the first cavity and second cavity are configured to interface with the harness.

15. The apparatus of claim 12, wherein the wicking member has a groove between the first portion and the second portion, wherein the groove is configured to interface with the slot of the housing to maintain the wicking member within the slot.

16. The apparatus of claim 12, wherein the wicking member is configured to disperse a liquid from within the cavity from the first portion of the wicking member to the second portion of wicking member.

17. The apparatus of claim 13, wherein the liquid is a scent agent.

18. The apparatus of claim 13, wherein the harness is parabolic in configuration.

19. The apparatus of claim 11, wherein cavity includes an interior wicking member, wherein the interior wicking member is configured to maintain the liquid within the cavity and limit the amount of liquid that exits through the slot.

20. A method of distributing a scent across an area, the method comprising a device of claim 11, the steps comprising:
    dragging the device across a ground surface, as is herein shown and described.

* * * * *